United States Patent [19]

Saksena

[11] Patent Number: 5,403,351
[45] Date of Patent: Apr. 4, 1995

[54] METHOD OF TRANSVENOUS DEFIBRILLATION/CARDIOVERSION EMPLOYING AN ENDOCARDIAL LEAD SYSTEM

[76] Inventor: Sanjeev Saksena, 33 Fairway Dr., Green Brook, N.J. 08812

[21] Appl. No.: 3,081

[22] Filed: Jan. 11, 1993

[51] Int. Cl.$^6$ ............................................. A61N 1/39
[52] U.S. Cl. ............................................. 607/4; 607/5
[58] Field of Search ...................... 607/4, 5, 123, 122, 607/119, 116

[56] References Cited

U.S. PATENT DOCUMENTS

| | | | |
|---|---|---|---|
| 3,995,623 | 12/1976 | Blake et al. | 128/642 |
| 4,106,512 | 8/1978 | Bisping | 128/418 |
| 4,528,203 | 10/1985 | Tacker et al. | 128/419 D |
| 4,641,656 | 2/1987 | Smits | 128/419 D |
| 4,662,377 | 5/1987 | Heilman et al. | 128/419 D |
| 4,727,877 | 3/1988 | Kallock | 128/419 D |
| 4,817,608 | 4/1989 | Shapland | 128/419 P |
| 4,825,871 | 5/1989 | Cansell | 128/419 D |
| 4,830,006 | 5/1989 | Haluska | 128/419 PG |
| 4,884,567 | 12/1989 | Elliott | 128/303 R |
| 4,932,407 | 6/1990 | Williams | 128/419 D |
| 4,944,300 | 7/1990 | Saksena | 128/419 D |
| 4,953,551 | 9/1990 | Mehra et al. | 128/419 D |
| 4,969,463 | 11/1990 | Dahl et al. | 128/419 D |
| 4,991,603 | 2/1991 | Cohen et al. | 128/786 |
| 4,998,975 | 3/1991 | Cohen et al. | 128/419 D |
| 5,014,696 | 5/1991 | Mehra | 128/419 D |
| 5,042,143 | 8/1991 | Holleman | 29/825 |
| 5,048,521 | 9/1991 | Pless | 128/419 PG |
| 5,052,407 | 10/1991 | Hauser | 128/786 |
| 5,063,928 | 11/1991 | Grevis | 128/419 D |
| 5,107,834 | 4/1992 | Ideker et al. | 607/5 |
| 5,117,824 | 6/1992 | Keimel | 128/419 D |
| 5,129,392 | 7/1992 | Bardy | 128/419 D |
| 5,165,403 | 2/1991 | Mehra . | |
| 5,243,980 | 9/1993 | Mehra | 607/6 |

FOREIGN PATENT DOCUMENTS 9218198  10/1992  WIPO ...................... 607/5

OTHER PUBLICATIONS

"The PCD TM Tachyarrhythemia Control Device—Model 72171B—An Implantable Device For The Control Of Ventricular Arrhythmias Through Pacing, Cardioversion And Defibrillation", 74 pp., copyright 1990 by Medtronic, Inc.

Primary Examiner—William E. Kamm
Assistant Examiner—Kennedy J. Schaetzle
Attorney, Agent, or Firm—Kenyon & Kenyon

[57] ABSTRACT

The method comprises defibrillating or cardioverting a heart, employing either an implanted or an external defibrillation/cardioversion device capable of generating electrical shocks, by transvenously inserting into the lower left pulmonary artery a pulmonary arterial lead comprising a distal defibrillation electrode, sensing the occurrence of fibrillation or an arrhythmia, and defibrillating or cardioverting the heart by electrical shocks between such electrode and a transvenously-inserted additional defibrillation electrode. The additional defibrillation electrode may comprise a proximal defibrillation electrode located on the pulmonary arterial lead, with its distal end having been positioned in the right atrium/superior vena cava. Alternatively, the method comprises transvenously inserting a second lead comprising said additional electrode, and positioning the same in the right ventricle, the right atrium, or the superior vena cava. Sensing/pacing electrode means may be positioned in the right ventricle, and optionally also in the right atrium, for sensing and pacing the heart.

11 Claims, 1 Drawing Sheet

METHOD OF TRANSVENOUS DEFIBRILLATION/CARDIOVERSION EMPLOYING AN ENDOCARDIAL LEAD SYSTEM

The present invention relates to methods of defibrillating or cardioverting a human heart, in conjunction with a defibrillator device, by transvenously inserting a defibrillation electrode into a patient's lower left pulmonary artery, sensing when, if ever, fibrillation occurs, and defibrillating the heart by electrical shocks between at least two defibrillation electrodes. Additionally, the device may also serve as a cardioverter, and/or to sense and pace a patient's heart.

BACKGROUND PRIOR ART

Several patents describe methods of defibrillation of a heart employing an implanted device, wherein at least two electrode-bearing leads are inserted through the superior vena cava/right atrium of a patient's heart and the leads lodged in the heart or its adjacent blood vessels.

U.S. Pat. No. 4,641,656 (Smits) describes such a method in conjunction with its FIG. 15, wherein separate electrodes are disposed in the apex of the right ventricle, in the right atrium, and optionally in the coronary sinus.

U.S. Pat. No. 4,727,877 (Kallok) describes a defibrillation method in which there is inserted a first lead bearing a first pair of electrodes, both of which are located in the right ventricle, and a second pair of electrodes located in the superior vena cava. A second lead, bearing an electrode at its distal end which is lodged in the coronary sinus, is inserted. The implanted device can deliver sequential pulses for purposes of the method of defibrillation.

U.S. Pat. No. 4,932,407 (Williams) describes a defibrillation method wherein a first lead having a distal defibrillation electrode is inserted into the right atrium, and a second lead bearing a distal defibrillation electrode at its distal end is inserted through the superior vena cava/right atrium into the coronary sinus and into the great vein.

U.S. Pat. No. 5,140,696 (Mehra) describes a method of defibrillation wherein a first lead having a distal defibrillation electrode is inserted into the right ventricle, and a second lead bearing a distal defibrillation electrode at its distal end is inserted through the superior vena cava/right atrium into the coronary sinus and into the great vein.

A number of designs are known for electrodes for use with devices and electrode-bearing leads that are inserted into the heart through the superior vena cava/right atrium, for example, U.S. Pat. No. 4,106,512 (Bisping), U.S. Pat. No. 5,042,143 (Holleman & Viktora) and U.S. Pat. No. 5,052,407 (Hauser, et al.).

The design and characteristics of implanted devices for use in methods of defibrillating, and generally also cardioverting, a human heart, optionally with the sensing and pacing thereof, are known in the prior art. Illustrative of these are U.S. Pat. No. 4,830,006 (Haluska, et al.), U.S. Pat. No. 4,969,463 (Dahl, et al.), U.S. Pat. No. 5,048,521 (Pless, et al.), U.S. Pat. No. 5,063,928 (Grevis, et al.), U.S. Pat. No. 5,117,824 (Keimel, et al.) and U.S. Pat. No. 5,129,392 (Bardy & Mehra). U.S. Pat. No. 4,953,551 (Mehra and Combs) describes a defibrillator having circuitry for generating biphasic pulses. These patents illustrate the variations in the circuitry, and the number of combinations and permutations in functions that can be performed, and the electrical wave forms and phases that may be employed.

An example of a currently available, specific implantable device is identified as PCD model 72171B. It is described in a technical manual entitled "THE PCD ® TACHYARRHYTHMIA CONTROL DEVICE—Model 72171B—An Implementable Device For The Control Of Ventricular Arrhythmias Through Pacing, Cardioversion, And Defibrillation," 74 pp., copyright 1990 by Medtronic, Inc., Minneapolis, Minn. 55432.

A number of patents describe various wave forms, electrical phases of the shock being administered, and the sequences of the shocks. Illustrative of these are U.S. Pat. No. 4,548,203 (Tacker, et al. ), U.S. Pat. No. 4,944,300 (Saksena) describing bi-directional shocks, and the above-identified U.S. Pat. No. 4,969,463 (Dahl, et al.).

The disclosure of each of the prior art references identified in the four preceding paragraphs are herewith incorporated by this express reference to them.

SUMMARY OF THE INVENTION

This invention is directed to a method of defibrillating or cardioverting a human heart, employing a defibrillation/cardioversion device.

The device may be located external to the body of a human, and when so located, is typically employed for relatively short-term or emergency use in a hospital. It is electrically powered, and comprises circuitry adapted to generate an electrical shock between typically two, but optionally more, defibrillation electrodes of opposing polarity as described hereinafter. Such devices are known, having been employed in hospitals for at least several years.

The device may also be implanted in the body of the human; it is typically employed in ambulatory patients. An implanted device comprises at least a source of electrical energy and circuitry adapted to generate an electrical shock between at least two defibrillation electrodes of opposing polarity. In addition, the device comprises circuitry adapted to sense the occurrence of fibrillation in said heart and in response thereto, generate such an electrical shock. The device also comprises a plurality of connecting terminals adapted to be electrically connected to at least one of the various electrodes described hereinafter. An implanted device may also function as a cardioverter, and may optionally also function to sense and pace the heart.

The method of defibrillating or cardioverting a human heart broadly comprises transvenously inserting a pulmonary arterial lead into a human's lower left pulmonary artery or a branch thereof. The lead comprises a distal defibrillation electrode, the distal end of which is disposed at or close to the distal tip of the pulmonary arterial lead. Such electrode is electrically connected to a terminal of the defibrillation device. The occurrence, if any, of fibrillation or an arrhythmia is sensed, and thereupon the heart is defibrillated or cardioverted by at least one electrical shock between such distal defibrillation electrode and at least one additional defibrillation electrode, the distal end of which has been positioned in the right ventricle, right atrium or superior vena cava. The additional defibrillation electrode is electrically connected to the defibrillation device in a polarity opposed to the polarity of the distal defibrillation electrode comprising part of the pulmonary arterial lead.

BRIEF DESCRIPTION OF THE FIGURE

FIG. 1 depicts right atrium 12, right ventricle 14, left ventricle 16, lower left pulmonary artery 18 and its branches, first branch artery 20, second branch artery 22 and third branch artery 24. FIG. 1 depicts a pulmonary arterial lead 26, and a second electrode lead 28, each comprising components described hereinafter. Individual electrodes are connected via various connecters 30 and 32 to terminals of a defibrillation device 34.

DESCRIPTION OF THE PREFERRED EMBODIMENT

Figure 1:
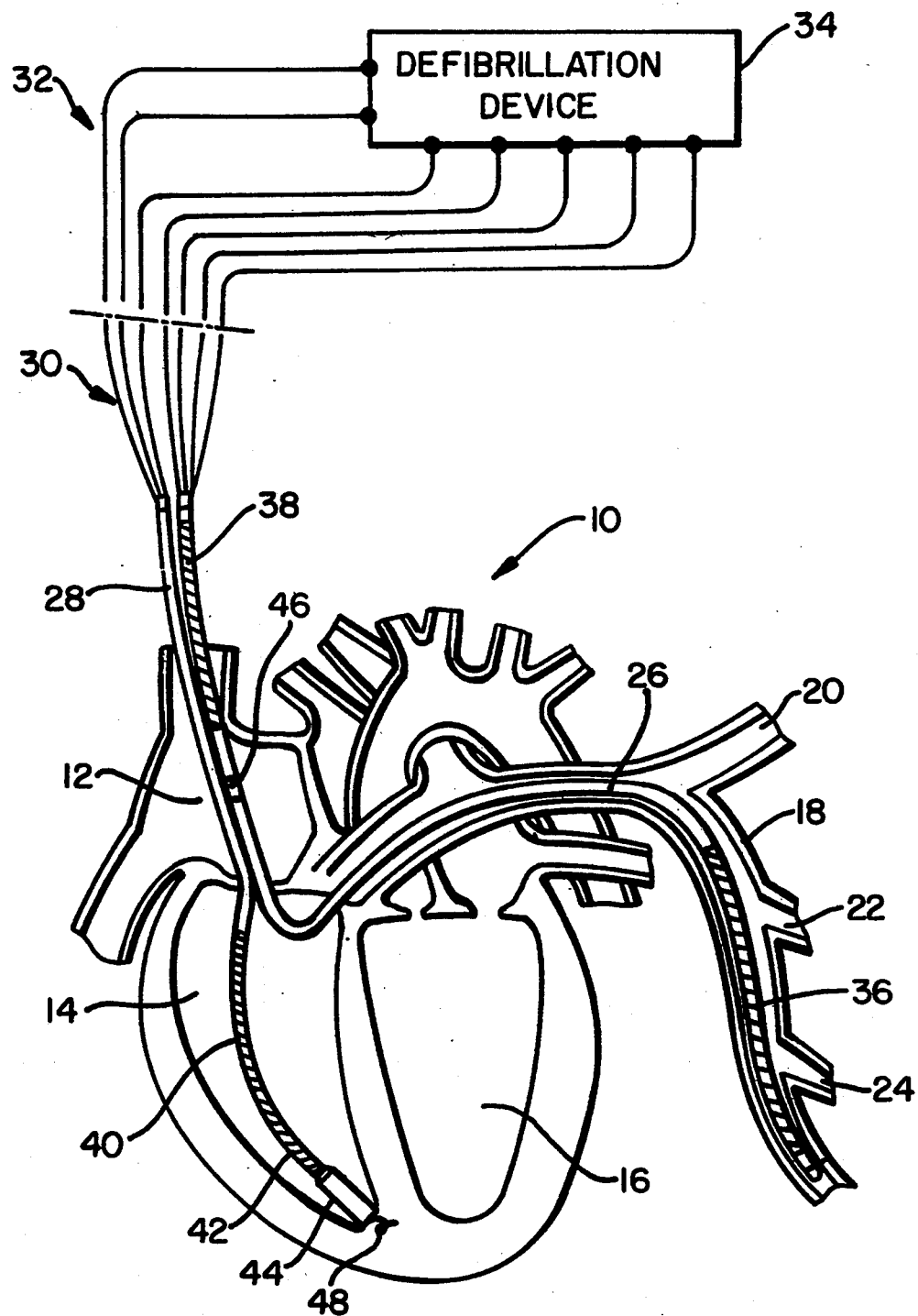
FIG. 1 is a schematic vertical sectional sketch of a human heart 10 and its adjacent arteries and veins, together with the right ventricle and pulmonary arterial leads as described herein.

With an implanted device, the method comprises transvenously inserting the distal end of pulmonary arterial lead 26 into the lower left pulmonary artery 18. Pulmonary arterial lead 26 comprises distal defibrillation electrode 36, the distal end of which is positioned during the process in the lower left pulmonary artery or in a branch thereof. Distal defibrillation electrode 36 is electrically connected via a pair of connectors 30 and 32 to an appropriate terminal of the device 34.

The distal tip of pulmonary arterial lead 26 is preferably lodged in the lower left pulmonary artery at a point inferior to second branch artery 22. A specific alternative embodiment is to lodge the distal tip of pulmonary arterial lead 26 in first branch artery 20.

In this embodiment, pulmonary arterial lead 26 also comprises a proximal defibrillation electrode 38, located on pulmonary arterial lead 26 proximal to distal defibrillation electrode 36, with the distal end of proximal electrode 38 being positioned during the process in right atrium 12 and/or in the superior vena cava, preferably the former. Proximal electrode 38 is also electrically connected to an appropriate terminal of the implanted defibrillation device, and is of the same polarity as distal defibrillation electrode 36.

The method further comprises transvenously inserting a second electrode lead 28, comprising an additional defibrillation electrode 40, into right ventricle 14 of the heart, and positioning the distal end of additional electrode 40 in the right ventricle of the heart, preferably at the apex thereof. Additional electrode 40 is electrically connected via a pair of connectors 30 and 32 to an appropriate terminal of the implanted device, and in a polarity opposed to the polarity of pulmonary arterial distal defibrillation electrode 36.

The third step comprises sensing the occurrence, if any, of defibrillation or an arrhythmia in the heart, and thereupon defibrillating or cardioverting the heart by at least one electrical shock, and normally a plurality of shocks, between, on the one hand, distal defibrillation electrode 36 and/or proximal defibrillation electrode 38, and, on the other hand, additional defibrillation electrode 40.

The shocks may be concurrent (i.e., simultaneous) between both of electrodes 36, 38, and additional electrode 40. Alternatively and generally preferably, the shocks may be sequential, i.e., alternating between the distal defibrillation electrode 36 and additional defibrillation electrode 40, and then between proximal electrode 38 and electrode 40.

As employed herein, the phrase "lower left pulmonary artery" is defined to mean that portion of the left pulmonary artery system extending from just prior to the bifurcation of first branch artery 20 from the lower left pulmonary artery, to a point inferior to (i.e., downstream from) the bifurcation of third branch artery 24 from the lower left pulmonary artery. The phrase "or branches thereof" when used in conjunction with the phrase "lower left pulmonary artery" embraces first branch artery 20, second branch artery 22 and third branch artery 24.

In the preferred embodiment of the method being here described and also in the various other embodiments described hereinafter, the applicable process variables, such as number of shocks to be employed, the duration of various shocks, and the amount of energy to be employed in a shock, are controlled by the circuitry and any variable settings of the defibrillation device, and the possible ranges and/or specific values of such variables are to be determined by the attending surgeon or physician.

The implanted device may be selected, or adapted, from those identified in the seventh to ninth paragraphs under the heading of Background Prior Art. The general criteria are that the implanted device have the features of capability of generating mono-, multi-, or poly-phase shocks (e.g., bi-phasic and/or multi-phasic shocks when proximal electrode 38 is employed, and mono-phasic shocks in any embodiment when electrode 38 is not employed), programmability, automatic gain sensing, dual chamber spacing and sensing, and bi-polar pacing and sensing.

Distal defibrillation electrode 36, and, when employed, proximal defibrillation electrode 38 are typically electrically connected anodally, with the additional defibrillation electrode 40 being electrically connected cathodally. However, the polarity may be reversed if desired. In addition, the polarity may be reversed between sequential shocks or groups of shocks during the defibrillation process. Although not a preferred embodiment, in a lead system comprising three defibrillation electrodes, proximal defibrillation electrode 38 optionally may be electrically connected to the device 10 in a polarity common to additional defibrillation electrode 40 and opposing the polarity of distal defibrillation electrode 36.

In the preferred embodiment, the method of the invention may also comprise sensing and pacing the heart. When this feature is practiced, at least one sensing/pacing electrode means is employed. Such electrode means is typically located near the distal end of second electrode lead 28, and may comprise a ring electrode 42, located distal to defibrillation electrode 40, together with an advanceable electrode 44, which is located distal to ring electrode 42. A suitable advanceable electrode is described in U.S. Pat. No. 4,106,512. Electrodes 42 and 44 are electrically insulated from each other, and electrically connected via a pair of separate connectors 30 and 32 to appropriate terminals of the implanted device.

In this preferred embodiment, the sensing/pacing electrode means also comprises a pair of split-ring sensing/pacing electrodes 46 positioned on pulmonary arterial lead 26 and disposed in right atrium 12, distal to and close to the proximal defibrillation electrode 38.

In an alternative advantageous embodiment, a second pair (not depicted) of split-ring sensing/pacing electrodes replaces electrodes 42 and 44, and is located at the distal end of the second electrode lead 28, and distal to and close to the additional defibrillation electrode 40.

As employed herein, "split-ring" refers to semi-circular electrodes (having a low length-to-diameter ratio) and also to semi-cylindrical electrodes (having a ratio of length-to-diameter approaching unity or greater than unity), arranged in pairs, each half of a pair electrically isolated from the other half and each half being electrically connected to an appropriate terminal of the implanted device. A split-ring electrode may also be segmented, e.g., the portion of the electrode electrically connected to the implanted device may subtend an arc of less than 180 angular degrees, e.g., 90 degrees. The respective semi-circular or semi-cylindrical halves may also be displaced transversely (i.e., staggered) along an electrode lead.

The split-ring electrodes described herein are typically small, e.g., about 3 mm in outer diameter and may vary in length from about 0.1 to about 10 mm in length. They are desirably located not more than about 5 mm from the defibrillation electrode to which they are adjacent.

ALTERNATIVE EMBODIMENTS

The invention embraces a plurality of alternative embodiments involving only two defibrillation electrodes in which the location of the additional defibrillation electrode 40 is varied. In all such alternative embodiments, the additional defibrillation electrode 40 is connected to device 34 in a polarity opposite to the polarity to the distal defibrillation electrode 36.

In the first of these alternative embodiments, the pulmonary arterial lead 26 is the only electrode lead. It comprises the additional defibrillation electrode 40, with the distal end thereof so located on pulmonary arterial lead 26 to be positioned during the method in the right atrium or superior vena cava, in a manner analogous to the location and positioning of the proximal defibrillation electrode 38 as described above with reference to the preferred embodiment. In this alternative embodiment, sensing/pacing electrode means may be employed, located on the pulmonary arterial lead 26 distal to the additional defibrillation electrode 40 and positioned in the right atrium.

The foregoing embodiment is useful when an external device is employed, as for instance, in a hospital, or, when employing an implanted device, the habitus (i.e., physical characteristics) of the patient renders undesirable or impractical the use of two transvenously inserted electrode leads.

The remaining embodiments employ two leads, with each comprising a single defibrillation electrode. Each such embodiment employs pulmonary arterial lead 26 comprising distal defibrillation electrode 36, as described above. In the first variation, the second electrode lead 28 comprises additional defibrillation electrode 40, which is located on that lead at its distal end and with the distal end of said electrode 40 being positioned during the process in the right atrium or the superior vena cava, analogous to the position of the proximal defibrillation electrode 38 in the preferred embodiment. The second electrode lead 28 or the pulmonary arterial lead 26 may also comprise sensing/pacing electrode means, e.g., as a split-ring electrode means 46. If on lead 28, it is located distal to and near additional defibrillation electrode 40, and when located on either lead, it is preferably positioned in the right atrium.

In a variation of the foregoing, the location on the second lead 28 of the additional defibrillation electrode 40 remains substantial the same, and so also is its position relative to the right atrium and superior vena cava, but the second lead is longer, with its distal end positioned in the right ventricle 14, preferably near the apex thereof. A sensing/pacing electrode means, if employed, is advantageously located at the distal tip of the second electrode lead 28 and positioned in the right ventricle 14. This would be in lieu of the sensing/pacing means described in the preceding paragraph as being located on the second lead 28, or in addition to or in lieu of the sensing/pacing electrode means described above as being located on pulmonary arterial lead 26.

Finally, in a third variation, the distal end of the second lead 28 is also positioned at or near the apex of the right ventricle 14. However, the distal end of the additional defibrillation electrode 40 is located close to the end of second lead 28, and positioned during the process in the right ventricle, as described above in connection with the preferred embodiment. Advantageously, a sensing/pacing electrode means is located at the distal end of second lead 28, distal to the distal end of the additional defibrillation electrode. In addition, the pulmonary arterial lead 26 and/or the second lead 28 may also comprise a sensing/pacing electrode means located in the right atrium 12.

In any of the foregoing alternative embodiments, the electrical shocks are mono-directional, either single or sequential shocks. Typically, a plurality of shocks of short duration are employed. The device 34 may be designed to reverse the polarity of the defibrillation electrodes between individual or groups of electrical shocks.

RELATED INFORMATION

Stylettes are employed in inserting pulmonary arterial lead 26 and second electrode lead 28. They are inserted under fluoroscopic guidance.

A large curved fine stylette is employed for positioning pulmonary arterial lead 26. The stylette is advantageously equipped with a flange arm at its proximal end for more readily applying torque when directing the distal tip of the lead to the right ventricle inflow tract, then into the left main pulmonary trunk artery, and then into the lower left pulmonary artery. The flange arm may be an integral part of or be affixed to the lead, with the axis of the flange approximately perpendicular to the longitudinal axis of the lead. A very fine straight stylette may be employed for inserting pulmonary arterial lead 26 and may optionally be left in situ for lead stabilization.

Two fine straight or curved (a 90° right angle curve) stylettes may be employed for positioning the distal tip of the second lead 28 at the apex of the right ventricle, either anterior or posterior. The proximal end of each such stylette advantageously may be equipped with a flanged arm as described above. A stabilization stylette may also be employed. It may consist of a fine, preformed, L-shaped stylette with the two arms that form the L subtending an angle of about 120 angular degrees, with the junction of the two arms being about 1-3 cm proximal to the proximal end of additional defibrillation electrode 40.

The distal end of second defibrillation lead 28 may be equipped with an active fixation means, such as a tine or screw-in apparatus (e.g., having a pigtail shape), enabling such distal end to be securely positioned, e.g., against the wall of the right ventricle, preferably at the apex thereof, either anterior or posterior. Screw-in apparatus 48 is depicted in FIG. 1. The distal end of pulmonary arterial lead 26 also is advantageously equipped with an active fixation means, thereby enabling such distal end to be secured against, or affixed to, the interior wall of the lower left pulmonary artery or a branch thereof.

The dimensions, and desired locations, of the apparatus, especially the defibrillation electrodes, with which the method is practiced depend on the habitus of the patient. Since the habitus of individual patients varies, the selection of specific dimensions and locations of the apparatus is the responsibility of the attending surgeon or physician. What follows are guidelines and approximations.

The length of distal pulmonary arterial defibrillation electrode 36 may be in the range of approximately 10 to about 20 cm. The distal end is desirably located within 5 mm of any active fixation means located at the distal end of lead 26.

The length of proximal pulmonary arterial electrode 38 may be in the range of approximately 10 to about 15 cm. The distal end of electrode 38 may be in the range of from approximately 45 to about 70 cm from the distal tip of the pulmonary arterial lead 26.

The length of the additional defibrillation electrode 40 may be in the range of from about 5 to 15 cm.

Any of the defibrillation electrodes may comprise two layers of coil-wound woven mesh of stainless steel, titanium or other suitable electrode material mounted on a No. 4 to No. 6 French lead body. Optionally, any of such electrodes may be as described and depicted in U.S. Pat. No. 5,042,143.

Having thus described the invention, what is claimed is:

1. A method of defibrillating a ventricular arrhythmia or cardioverting the heart of a human by employing an electrically-powered device comprising connecting terminals, said terminals being adapted to be electrically connected to at least one of the electrodes defined hereinafter, and circuitry adapted to sense the occurrence of fibrillation or an arrhythmia occurring in a ventricle of said heart and in response thereto, generate an electrical shock between at least two of the defibrillation electrodes of opposing polarity as defined hereinafter, which method comprises:
   A. transvenously inserting the distal end of a pulmonary arterial lead into said human's lower left pulmonary artery or a branch thereof, said pulmonary arterial lead comprising a distal pulmonary arterial defibrillation electrode, the distal end of which is disposed an or close to the distal tip of said pulmonary arterial lead, said distal pulmonary arterial defibrillation electrode being electrically connected to an appropriate terminal of said device,
   B. transvenously inserting the distal end of a second lead through the right atrium and into the right ventricle of said heart, said second lead comprising said at least one ventricular defibrillation electrode located at or near the distal end thereof, and positioning at least a portion of said ventricular defibrillation electrode in or near the apex of said right ventricle, said ventricular defibrillation electrode being connected to an appropriate terminal of said device in a polarity opposed to the polarity of said pulmonary arterial defibrillation electrode,
   C. sensing the occurrence, if any, of ventricular fibrillation or arrhythmia in said heart; and
   D. thereupon defibrillating or cardioverting said heart by at least one electrical shock between said distal pulmonary arterial defibrillation electrode and said ventricular defibrillation electrode.

2. The method of claim 1, wherein said second lead comprises sensing/pacing electrode means located at the distal end of said second lead, and distal to said ventricle defibrillation electrode.

3. The method of claim 1, wherein the distal tip of said pulmonary arterial lead is positioned in the lower left pulmonary artery inferior to the second branch artery.

4. The method of claim 1, wherein the distal tip of said pulmonary arterial lead is inserted into and positioned in the first branch artery of said human.

5. The method of claim 1, wherein said device has been previously implanted in said human.

6. The method of claim 1, wherein said pulmonary arterial lead comprises said one additional defibrillation electrode located proximal to said distal pulmonary arterial defibrillation electrode, and wherein said method comprises positioning the distal end of said additional defibrillation electrode in the right atrium or in the superior vena cava of said human, said additional defibrillation electrode being electrically connected to said device in a polarity common to the polarity of said distal pulmonary arterial defibrillation electrode.

7. The method of claim 6, wherein said pulmonary arterial lead comprises sensing/pacing electrode means located means closely adjacent to said additional defibrillation electrode.

8. The method of claim 1, wherein defibrillation is accomplished by bi-directional shocks between said defibrillation electrode on said pulmonary arterial lead, and said ventricular defibrillation electrode.

9. The method of claim 8, wherein said bi-directional shocks are sequential.

10. The method of claim 8, wherein said shocks are multi-phasic.

11. The method of claim 1, wherein said second lead comprises sensing/pacing electrode means located closely adjacent and distal to said ventricular defibrillation electrode, and said sensing/pacing electrode means is connected to appropriate terminals of said device, which method further comprises pacing said heart in response at least in part to electrical signals from said sensing/pacing electrode means.

* * * * *